United States Patent
Tamura et al.

(10) Patent No.: US 8,580,284 B2
(45) Date of Patent: Nov. 12, 2013

(54) OIL-BASED COSMETIC PREPARATION

(75) Inventors: Eiko Tamura, Sumida-ku (JP); Kouji Ohsaki, Wakayama (JP); Kazuo Kuwahara, Wakayama (JP); Kazuhiro Ishikawa, Sumida-ku (JP); Kenko Kurita, Sumida-ku (JP); Yu Saito, Sumida-ku (JP)

(73) Assignee: Kao Corporation, Tokyo (JP)

( * ) Notice: Subject to any disclaimer, the term of this patent is extended or adjusted under 35 U.S.C. 154(b) by 95 days.

(21) Appl. No.: 13/120,713

(22) PCT Filed: Sep. 24, 2009

(86) PCT No.: PCT/JP2009/067137
§ 371 (c)(1),
(2), (4) Date: Mar. 24, 2011

(87) PCT Pub. No.: WO2010/035893
PCT Pub. Date: Apr. 1, 2010

(65) Prior Publication Data
US 2011/0177143 A1    Jul. 21, 2011

(30) Foreign Application Priority Data

Sep. 25, 2008  (JP) ................................ 2008-245529
Aug. 6, 2009   (JP) ................................ 2009-183266
Aug. 6, 2009   (JP) ................................ 2009-183267

(51) Int. Cl.
*A61K 8/02*     (2006.01)
*A61K 31/715*   (2006.01)

(52) U.S. Cl.
USPC ........................................... 424/401; 514/57

(58) Field of Classification Search
None
See application file for complete search history.

(56) References Cited

U.S. PATENT DOCUMENTS

| 6,417,323 | B1 | 7/2002 | Miyanaga et al. | |
|---|---|---|---|---|
| 7,226,503 | B2 * | 6/2007 | Anselmann et al. | 106/489 |
| 2005/0112161 | A1 * | 5/2005 | Luo et al. | 424/401 |
| 2006/0062749 | A1 | 3/2006 | Shelton et al. | |
| 2007/0104667 | A1 | 5/2007 | Mondet et al. | |

FOREIGN PATENT DOCUMENTS

| CA | 2 087 488 | 7/1993 |
|---|---|---|
| GB | 1 134 170 | 11/1968 |
| JP | 8 175929 | 7/1996 |
| JP | 2006-219486 | 8/2006 |
| JP | 2008-106003 | 5/2008 |
| JP | 2008-513480 | 5/2008 |
| JP | 2010-059408 | 3/2010 |
| WO | WO 2006/034071 A1 | 3/2006 |

OTHER PUBLICATIONS

JP2007-277108, Machine Translation, 2007.*
JP2007-277108, Partial Human Translation, 2007.*
Sigma-Aldrich, Silica MSDS, 2012.*
International Search Report Issued Nov. 23, 2010 in PCT/JP09/067137 filed Sep. 24, 2009.

* cited by examiner

*Primary Examiner* — Blessing Fubara
*Assistant Examiner* — Jennifer Berrios
(74) *Attorney, Agent, or Firm* — Oblon, Spivak, McClelland, Maier & Neustadt, L.L.P.

(57) ABSTRACT

Abstract Provided is an oil-based cosmetic preparation which retains a smooth feel. Provided is an oil-based cosmetic preparation containing the following components (A), (B), and (C): (A) a cellulose derivative having a cellulose skeleton in a main chain, in which 67 mol % or more in total hydroxyl groups are substituted with a group —O-M-R, wherein M represents $CH_2$ or a carbonyl group $C=O$, and R represents a straight or branched alkyl or alkenyl group having 3 to 40 carbon atoms; (B) an ester oil which is liquid at 25° C.; and (C) a hydrocarbon oil which is liquid at 25° C., in which a weight ratio (B)/(C) of the component (B) to the component (C) is 8/1 to 1/4.

14 Claims, No Drawings

OIL-BASED COSMETIC PREPARATION

CROSS REFERENCES TO RELATED APPLICATIONS

This application is a 371 of International Patent Application No. PCT/JP2009/067137, filed on Sep. 24, 2009, and claims priority to Japanese Patent Application No. 2008-245529, filed on Sep. 25, 2008, and Japanese Patent Application No. 2009-183266, filed on Aug. 6, 2009, Japanese Patent Application No. 2009-183267, filed on Aug. 6, 2009.

FIELD OF THE INVENTION

The present invention relates to an oil-based cosmetic preparation.

BACKGROUND OF THE INVENTION

An oil-based cosmetic preparation can protect the lip and skin from dryness and impart a smooth feel to the lip and the skin by applying the oil-based cosmetic preparation onto the lip and the skin. However, although an oil solution having a high viscosity may provide a good existing feel of the cosmetic upon application to the skin, such an oil solution has problems of becoming greasy easily and being difficult to spread. Meanwhile, an oil solution having a low viscosity has a poor existing feel, and not only can not retain the smooth feel but also easily loses the good existing feel of the cosmetic upon application to the skin. Those problems are particularly remarkable in a lip cosmetic preparation.

It has been known that a smooth feel can be imparted by blending an aqueous polymer having a large molecular weight in water-based cosmetic preparations such as face lotions, o/w type milky lotions, and massage agents. Likewise in the oil-based cosmetic preparation, it has been attempted that the oil-based cosmetic preparation is modified by using a polymer compound having a large molecular weight (cellulose derivatives and the like) (e.g., Patent Documents 1 and 2). However in Patent Documents 1 and 2, inhibition of secondary adherence of the oil-based cosmetic preparation is disclosed, but modification of the pleasant feel upon application to the skin is not disclosed.

On the other hand, it is possible to enhance the smooth feel by using polyisoprene and polyether (e.g., Patent Document 3). However, a strong stringy property occurs upon the application of the oil-based cosmetic preparation when such a polymer compound is used.

Further, Patent Document 4 discloses oil-soluble polysaccharide palmitate, and describes that the oil-soluble polysaccharide palmitate may also be used as an oil-based thickener for cosmetics.

[Patent Document 1] JP-A-2007-527861
[Patent Document 2] JP-A-08-175929
[Patent Document 3] WO 99/42513
[Patent Document 4] JP-A-05-255401

SUMMARY OF THE INVENTION

The present invention provides an oil-based cosmetic preparation including the following components (A), (B), and (C):

(A) a cellulose derivative having a cellulose skeleton in a main chain, in which 67 mol % or more in total hydroxyl groups are substituted with a group —O-M-R, wherein M represents $CH_2$ or a carbonyl group $C=O$, and R represents a straight or branched alkyl or alkenyl group having 3 to 40 carbon atoms;

(B) an ester oil which is liquid at 25° C.; and
(C) a hydrocarbon oil which is liquid at 25° C., in which a weight ratio (B)/(C) of the component (B) to the component (C) is 8/1 to 1/4.

DETAILED DESCRIPTION OF THE INVENTION

The present invention provides an oil-based cosmetic preparation which provides and retains a smooth feel.

The inventors of the present invention have found that an oil-based cosmetic preparation which provides and retains a smooth feel by using a particular cellulose derivative in combination with a liquid ester oil and a liquid hydrocarbon oil at a particular ratio.

The oil-based cosmetic preparation of the present invention especially spreads well and feels and fits comfortably upon application to the skin, which is different from a simple smoothness of an oil solution, and retains a unique smooth feel to the skin. A non-sticky feeling and pleasant feel upon application to the skin are also retained. "A comfortable feel and fit upon application to the skin" is here in also referred to as "compatibility upon application". "A pleasant feel upon application to the skin" is herein also referred to as "application feeling".

The above-mentioned Patent Document 4 has disclosed only an extremely broad range of 0.5 to 50.0 of an infrared absorption ratio (ratio of a peak at 1,734 $cm^{-1}$ to a peak at 3,470 $cm^{-1}$) as a preferred degree of esterification. In Patent Document 4, only an intended use as a thickener is also shown, and it is not disclosed at all that the smooth feel is obtained by using the cellulose derivative having a particular structure together with the ester oil and the hydrocarbon oil at a particular ratio as disclosed in the subject application.

The cellulose derivative containing as the component (A) to be used in the present invention is not limited as long as the cellulose derivative has a cellulose skeleton in its main chain. Examples of the raw material cellulose derivative include cellulose, and preferably include short-chain acylated cellulose such as acetyl cellulose and acetylbutyl cellulose, and cellulose modified with a hydroxyalkyl group, a glyceryl ether group, or a (mono)alkyl glyceryl ether group. More specific examples include hydroxyethyl cellulose, hydroxypropyl cellulose, hydroxypropylmethyl cellulose, glyceryl cellulose, and methylglyceryl cellulose.

Further, those having the following constitution unit are preferred as a raw material cellulose derivative.

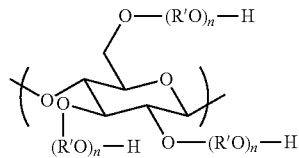

(wherein R' represents a straight or branched alkylene group having 2 to 8 carbon atoms, and "n" represents a numeral so that an average addition mole number of R'O per glucose unit is 0.1 to 10.)

In the constitution unit, R' is preferably a straight or branched alkylene group having 2 to 4 carbon atoms, and more preferably an ethylene group or a propylene group. As "n", the numeral can be selected so that the average addition mole number of R'O per glucose unit is preferably 0.3 to 5, more preferably 0.5 to 4.5, and even more preferably 1 to 4.

The preferred raw material cellulose derivative includes hydroxyethyl cellulose and hydroxypropyl cellulose, and hydroxypropyl cellulose is preferred.

A weight average molecular weight (Mw) of the raw material cellulose derivative is preferably 10,000 to 4,000,000, more preferably 100,000 to 3,000,000, and even more preferably 500,000 to 2,000,000 in terms of solubility in the oil solution and feel.

In the group —O-M-R which is a substituent of a hydroxyl group in the raw material cellulose derivative, M represents $CH_2$ or a carbonyl group C=O, and R represents a straight or branched alkyl or alkenyl group having 3 to 40 carbon atoms.

(i) Examples of the linear alkyl group include a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, a tetracosyl group, a pentacosyl group, a hexacosyl group, a heptacosyl group, an octacosyl group, a nonacosyl group, a triacontyl group, a hentriacontyl group, a dotriacontyl group, a tritriacontyl group, a tetratriacontyl group, a pentatriacontyl group, a hexatriacontyl group, a heptatriacontyl group, an octatriacontyl group, a nonatriacontyl group, and a tetracontyl group.

(ii) Examples of the branched alkyl group include a methylpentyl group, a methylhexyl group, a methylheptyl group, a methyloctyl group, a methylnonyl group, a methylundecyl group, a methylheptadecyl group, an ethylhexadecyl group, a methyloctadecyl group, a propylpentadecyl group, a 2-hexyldecyl group, a 2-octyldodecyl group, a 2-heptylundecyl group, a 2-decyltetradecyl group, a 2-dodecylhexadecyl group, a 2-tetradecyloctadecyl group, and a 2-octadecylbehenyl group.

(iii) Examples of the linear alkenyl group include a dodecenyl group, a tridecenyl group, a tetradecenyl group, a pentadecenyl group, a hexadecenyl group, a heptadecenyl group, an octadecenyl group, a nonadecenyl group, an icosenyl group, a henicosenyl group, a docosenyl group, a tricosenyl group, a tetracosenyl group, a pentacosenyl group, a hexacosenyl group, a heptacosenyl group, and an octacosenyl group.

(iv) Examples of the branched alkenyl group include an isotridecenyl group, an isooctadecenyl group, an isotriacontenyl group, a 2-butyloctenyl group, a 2-hexyldecenyl group, a 2-octyldodecenyl group, a 2-decyltetradecenyl group, and a 2-dodecylhexadecenyl group.

Of those, the straight alkyl group is preferred in terms of imparting smoothness when the oil-based cosmetic preparation is applied. Further, in terms of being easily spread and having good adhesiveness, the straight alkyl group has preferably 9 to 21, more preferably 11 to 17, and even more preferably 15 carbon atoms.

A substitution degree of the group —O-M-R which is substituted for the hydroxyl group is 67 mol % or more, preferably 70 mol % or more, and more preferably 80 mol % or more to 100 mol %. It is more preferred that the substitution rate of the group —O-M-R be high in terms of enhancing the solubility in the oil solution, but is preferred to be 90 mol % or less in terms of moist feeling and smoothness property. It is also preferred in terms of no roughness that hydroxyl groups remain appropriately. The amount of the remaining hydroxyl groups is preferably 2 to 33 mol % and more preferably 5 to 20 mol %.

The weight average molecular weight of the cellulose derivative as the component (A) is preferably 100,000 or more and more preferably 200,000 or more, and preferably 4,000,000 or less and more preferably 3,000,000 or less, and even more preferably 500,000 to 2,000,000 in terms of solubility and retaining the smooth feel.

Note that the weight average molecular weight (Mw) is determined by measurement using gel permeation chromatography (using a calibration curve determined using chloroform as a solvent and straight polystyrene as standards, and a differential refractive index detector).

Such a cellulose derivative is produced by reacting the raw material cellulose derivative with an acid halide having a straight or branched alkyl or alkenyl group having 4 to 40 carbon atoms to perform the substitution of 67 mol or more of the total hydroxyl groups in the raw material cellulose derivative.

A cellulose derivative in which M represents $CH_2$ can be produced by reacting a cellulose derivative with a corresponding alkyl halide or a sulfonate such as alkyl mesylate in the presence of a base. A cellulose derivative in which a main chain includes a cellulose skeleton can also be obtained by a transesterification reaction (acidolysis) of acetyl cellulose. According to the method, a cellulose ester derivative in which an amount of the remaining hydroxyl group is extremely small can be obtained.

Specific examples of the above cellulose ester derivative include: hydroxyethyl cellulose laurate, hydroxyethyl cellulose myristate, hydroxyethyl cellulose palmitate, hydroxyethyl cellulose stearate, and hydroxyethyl cellulose behenate; hydroxypropyl cellulose laurate, hydroxypropyl cellulose myristate, hydroxypropyl cellulose palmitate, hydroxypropyl cellulose stearate, and hydroxypropyl cellulose behenate; hydroxyethylmethyl cellulose laurate, hydroxyethylmethyl cellulose myristate, hydroxyethylmethyl cellulose palmitate, hydroxyethylmethyl cellulose stearate, and hydroxyethylmethyl cellulose behenate; and hydroxypropylmethyl cellulose laurate, hydroxypropylmethyl cellulose myristate, hydroxypropylmethyl cellulose palmitate, hydroxypropylmethyl cellulose stearate, and hydroxypropylmethyl cellulose behenate. Of those, hydroxypropyl cellulose laurate, hydroxypropyl cellulose myristate, hydroxypropyl cellulose palmitate, hydroxypropyl cellulose stearate, and hydroxypropyl cellulose behenate are preferred, and hydroxypropyl cellulose palmitate is more preferred.

One or more kinds of the cellulose derivatives as the component (A) can be used. The amount of the cellulose derivative to be contained in the oil-based cosmetic preparation of the present invention is preferably 0.1% by weight or more, more preferably 0.5% by weight or more, and particularly preferably 0.8% by weight or more, and preferably 20% by weight or less and more preferably 15% by weight or less. If the amount of the cellulose derivative is within the above-described range, the smoothness after application is retained longer in combination with the oil solution described later.

The component (B) is an ester oil which is a liquid at 25° C., for example, octyldodecyl myristate, isopropyl myristate, isopropyl isostearate, isononyl isononanoate, isotridecyl isononanoate, butyl stearate, oleyl oleate, octyldodecyl ricinoleate, neopentylglycol dicaprate, diisostearyl malate, octyl hydroxystearate, macadamia nut oil, olive oil, castor oil, jojoba oil, avocado oil, sunflower oil, and pentaerythrityl tetraoctanoate.

The ester oil as the component (B) is a good solvent for the cellulose derivative as the component (A), and is good for solubilizing the component (A). Further, the component (B)

is preferably a branched, saturated fatty acid ester because the cellulose derivative as the component (A) is easily dissolved therein.

Examples of branched, saturated fatty acid esters include isopropyl myristate, isopropyl isostearate, diisostearyl malate, isononyl isononanoate, isotridecyl isononanoate, 2-ethylhexyl palmitate, octyldodecyl myristate, octyldodecyl oleate, and octyldodecyl erucate. Branched fatty acid branched alcohol esters are preferred. Isononyl isononanoate and isotridecyl isononanoate are preferred, and isotridecyl isononanoate is more preferred.

One or more kinds of the ester oils as the component (B) can be used. The amount of the ester oil to be contained in the oil-based cosmetic preparation of the present invention is preferably 10 to 80% by weight and more preferably 20 to 60% by weight in terms of solubility of the cellulose derivative as the component (A) and sense upon use (spreading and compatibility upon application) of the oil-based cosmetic preparation.

The component (C) is a hydrocarbon oil which is liquid at 25° C., and includes straight or branched and alicyclic hydrocarbons. The number average molecular weight of the component (C) is preferably 170 to 5,000 and more preferably 250 to 3,000.

Specific examples of the hydrocarbon oil include light isoparaffin, liquid paraffin, liquid isoparaffin, heavy liquid isoparaffin, hydrogenated polyisobutene, hydrogenated polydecene, and squalane. Of those, hydrogenated polyisobutene is preferred in terms of retaining the smooth feel and enhancing application feel. A hydrocarbon oil having a number average molecular weight of preferably 1,000 to 4,000 and more preferably 1,300 to 2,700 is used.

The hydrocarbon oil as the component (C) preferably includes a hydrocarbon oil having a number average molecular weight of 1,000 to 5,000.

The hydrocarbon oil as the component (C) is preferably used in combination of two or more kinds as a mixture. It is more preferred to use liquid hydrocarbon oils each having a number average molecular weight of 700 or less and 600 or less, together with liquid hydrocarbon oils each having a number average molecular weight of 1,000 or more and 2,000 or more in mixture. It is even more preferred to use a liquid hydrocarbon oil having a number average molecular weight of 700 or less together with a liquid hydrocarbon oil having a number average molecular weight of 1,000 or more in mixture at a ratio of 1/2 to 2/1. This can provide unique smoothness which is different from the simple smoothness of an oil solution, and not only can retain the effect of unique smoothness but also can enhance application feeling, in a relationship of the components (A) and (B) described later.

One or more kinds of the hydrocarbon oils as the component (C) can be used. The amount of the hydrocarbon oil to be contained in the oil-based cosmetic preparation of the present invention is preferably 5 to 60% by weight and more preferably 15 to 40% by weight in total in terms of smoothness and application feeling of the oil-based cosmetic preparation.

The cellulose derivative as the component (A) is not satisfactory by merely being dissolved in the oil solution, and the smoothness upon application and the smoothness over time improve when the component (B) and the component (C) is mixed at a weight ratio (B)/(C) of 8/1 to 1/4. Further, the weight ratio (B)/(C) is preferably 5/1 to 1/3 and more preferably 2/1 to 1/2.

The total content of the component (B) and the component (C) varies depending on the dosage form of the oil-base cosmetic preparation, and is preferably 20 to 90% by weight and more preferably 50 to 90% by weight.

The oil-based cosmetic preparation of the present invention may further contain one or more paste oil solutions (D) selected from dimer acid esters, dimer diol derivatives, cholesterol fatty acid esters, phytosterol fatty acid esters, polyglycerine fatty acid esters, and pentaerythritol fatty acid esters, and the oil-based cosmetic preparation has excellent luster and feels smooth and provides a good sense upon use with a non-sticky feeling.

Those compounds exhibit an appearance and a characteristic of a paste form (liquid with high viscosity to semisolid) at 25° C. because the compounds are only partially crystallized. The reasons for this are because those compounds are a mixture of substances having a similar structure and their glass transition temperature is high because they are polycyclic compounds.

Examples of dimer acid esters include dimer dilinoleic acid dimer dilinoleyl bis(behenyl/isostearyl/phytosteryl) and dimer dilinoleic acid dimer dilinoleyl bis (phytosteryl/isostearyl/cetyl/stearyl/behenyl), and examples of commercially available products include Plandool-G and Plandool-H (both of which are manufactured by NIPPON FINE CHEMICAL CO., LTD.).

Examples of dimer dial derivatives include hydroxyalkyl (C12-14) hydroxy dimer dilinoleyl ether and hydroxyalkyl (C16-18) hydroxy dimer dilinoleyl ether, and examples of commercially available products include Supermol LM and Supermol PS (both of which are manufactured by Croda Japan KK).

Examples of cholesterol fatty acid esters include cholesteryl isostearate, cholesteryl hydroxystearate, macadamia nut fatty acid cholesteryl, and lanolin fatty acid cholesteryl, and examples of commercially available products include EXCEPARL IS-CE (manufactured by Kao Corporation), Salacos HS (manufactured by THE NISSHIN OILLIO GROUP, LTD.), and YOFCO MAC and YOFCO CLE-S (both of which are manufactured by NIPPON FINE CHEMICAL CO., LTD.).

Examples of phytosterol fatty acid esters include phytosteryl oleate, dimer dilinoleic acid dimer dilinoleyl bis (behenyl/isostearyl/phytosteryl), dimer dilinoleic acid (phytosteryl/isostearyl/setyl/stearyl/behenyl), and macadamia nut fatty acid phytosteryl, and examples of commercially available products include Salacos PO (manufactured by THE NISSHIN OILLIO GROUP, LTD.), and YOFCO MAS, Plandool-G, Plandool-S, and Plandool-H (all of which are manufactured by NIPPON FINE CHEMICAL CO., LTD.).

Examples of polyglycerine fatty acid esters include macadamia nut oil polyglyceryl and (isostearate/behenate)(gylcerin/polyglyceryl-6)esters, and examples of commercially available products include S Face, VL-211, and VL-212 (all of which are manufactured by SAKAMOTO YAKUHIN KOGYO CO., LTD.).

Examples of pentaerythritol fatty acid esters include hexahydroxy stearate dipentaerythrityl, (hydroxystearate/isostearate)dipentaerythrityl, and (hydroxystearate/stearate/rosinate)dipentaerythrityl, and examples of commercially available products include Cosmol 168M, Cosmol 168E, and Cosmol 168AR (all of which are manufactured by THE NISSHIN OILLIO GROUP, LTD.).

The component (D) has a crystallization temperature measured by DSC of preferably 20 to 55° C. and more preferably 23 to 45° C. In the measurement by DSC, the temperature is raised up to 120° C. at 10° C./min., which is then kept for 10 minutes, and then the temperature is lowered to −50° C. at 5° C./min. The crystallization temperature is the onset point of the exothermic peak during cooling.

One or more kinds of the components (D) can be used, and the amount of the component (D) to be contained in the oil-based cosmetic preparation of the present invention is preferably 0.5 to 50% by weight and more preferably 3 to 30% by weight in terms of imparting luster and sense upon use.

The weight ratio (A)/(D) of the component (A) to the component (D) is preferably 0.002 to 100, more preferably 0.01 to 50, and even more preferably 0.05 to 20 in terms of a non-sticky feeling upon application and over time.

The weight ratio (B)/(D) of the component (B) to the component (D) is preferably 0.2 to 160 and more preferably 0.5 to 30 in terms of good spread upon application and high luster after application.

The oil-based cosmetic preparation of the present invention may further contain a glittering powder (E) having an average particle diameter of 30 to 500 μm and preferably 40 to 400 μm, and the oil-based cosmetic preparation has an excellent glittering property and can retain the smooth feel.

As the glittering powder, a powder obtained by covering a plate substrate with a coating agent and a powder obtained by laminating multiple thin layers are used suitably.

The powder obtained by covering the plate substrate with the coating agent includes, for example, a powder obtained by covering the plate substrate having an average particle diameter of 30 to 500 μm with one or more kinds of coating agents selected from metals, metal oxide, and organic pigments.

Examples of plate substrates include mica, synthetic mica, silica flakes, glass flakes, alumina flakes, and metal aluminum flakes. Of the covering agents, examples of metals include gold, silver, and aluminum, examples of metal oxides include titanium oxide, zirconium oxide, aluminum oxide, iron oxide, silicon oxide, chromium oxide, and other metal complexes such as iron blue. Examples of the organic pigment include carmine, red color No. 202, blue color No. 1, yellow color No. 4, and ultramarine.

As the glittering powder as the component (E), a laminated powder having an average particle diameter of 30 to 500 μm can be used.

Examples of laminated powders include a polyethylene terephthalate/polymethylmethacrylate laminated powder, polyethylene terephthalate/polyethylene isophthalate laminated powder, polyethylene terephthalate/aluminum/epoxy laminated powder, polyethylene terephthalate/silver/epoxy laminated powder, polyethylene terephthalate/gold/epoxy laminated powder, polyethylene terephthalate/aluminum/urethane laminated powder, polyethylene terephthalate/silver/urethane laminated powder, polyethylene terephthalate/gold/urethane laminated powder, polyethylene terephthalate/urethane laminated powder, and polyethylene terephthalate/(polyethylene terephthalate/polyethylene isophthalate copolymer) laminated powder.

Various surface treatments such as a water-repellent treatment and a water-repellent/oil-repellent treatment may be given to those glittering powders by ordinary methods.

As examples of glittering powders as the component (E), commercially available products include Metashine MC1120RR, Metashine MC1120RB, Metashine MC1120RS, Metashine MC1120RY, Metashine MC1080RR, Metashine MC1080RB, Metashine MC1080RS, and Metashine MC1080RY (all of which are titanium oxide/silicic anhydride-coated glass manufactured by NIPPON SHEET GLASS CO., LTD.), Flamenco Sparkle Gold, Flamenco Sparkle Red, and Flamenco Sparkle Blue (all of which are titanium mica manufactured by Engelhard), Prominence SF, Prominence YF, Prominence RF, Prominence VF, Prominence GF, Prominence SH, Prominence YH, Prominence RH, and Prominence VH (all of which are titanium mica manufactured by Nihonkoken Co., Ltd.), PRESTIGE Twinkling Silver (titanium mica manufactured by ECKART GmbH), NEW Aurora Flake (19) Red and NEW Aurora Flake (16) Green (both of which are polyethylene terephthalate/polyethylene isophthalate laminated film powders manufactured by KAKUHACHI GYORINHAKU), DiamondPiece CO-3UC, CO-20UC, and CO-40UC (all of which are polyethylene terephthalate/aluminum/urethane laminated powders manufactured by Daiya Industry), and RAINBOW FLAKE II No. 55-S, No. 501-S, and No. 530-S (all of which are polyethylene terephthalate/polymethylmethacrylate laminated powders manufactured by Daiya Industry).

One or more kinds of the glittering powders as the component (E) can be used, and the amount of the glittering powder to be contained in the oil-based cosmetic preparation of the present invention is preferably 0.2 to 20%, by weight and more preferably 0.5 to 15% by weight in terms of high glittering property.

Further, the weight ratio (A)/(E) of the component (A) to the component (E) is preferably 0.01 to 150 and more preferably 0.05 to 20 in terms of good spread upon application and retaining smoothness.

Further, the weight ratio (B)/(E) of the component (B) to the component (E) is preferably 0.5 to 400 and more preferably 2 to 60 in terms of good spread upon application and a high glittering property.

The oil-based cosmetic preparation of the present invention may further contain branched fatty acids, higher alcohols, or silicone oil as a component for adjusting the feel of the cosmetic preparation. Examples of branched fatty acids include those having 10 to 32 carbon atoms such as isononanoate and isostearate. Examples of higher alcohols include those having 10 to 30 carbon atoms such as lauryl alcohol, isostearyl alcohol, and octyldodecanol. Examples of silicone oils include dimethylpolysiloxane, methylphenylpolysiloxane, dimethylcyclopolysiloxane, and methylhydropolysiloxane.

Further, a wax component may be used as a shape retaining agent. Examples of wax components include waxes derived from plants such as candellila wax, rice wax, carnauba wax, and tree wax; waxes derived from animals such as bee wax and whale oil; waxes derived from minerals such as montan wax, ozokerite, and ceresin; waxes derived from petroleum such as microcrystalline wax and paraffin wax; synthetic waxes such as hydrogenated castor oil, hydrogenated jojoba oil, 12-hydroxystearic acid, amide stearate, imide phthalic anhydride, and silicone wax; fatty acids such as laurate, myristate, palmitate, stearate, behenate, and fatty acid lanolate.

In addition, examples of color materials may include extender pigments, colorant pigments, and pearl pigments.

Examples of extender pigments include pigments such as inorganic compounds such as silicic acid, silicic anhydride, magnesium silicate, talc, sericite, mica, kaolin, clay, bentonite, bismuth oxychloride, zirconium oxide, magnesium oxide, aluminum oxide, calcium sulfate, barium sulfate, magnesium sulfate, calcium carbonate, and magnesium carbonate, and composite powders thereof.

Examples of colorant pigments include metal oxides such as titanium oxide, zinc oxide, yellow iron oxide, red iron oxide, black iron oxide, iron blue, ultramarine, chromium oxide, and chromium hydroxide, metal complexes such as manganese violet and cobalt titanate, and further, inorganic pigments such as carbon black, organic pigments such as tar-based colorants and lake pigments, and natural pigments such as carmine.

Examples of pearl pigments include mica, synthetic mica, glass, and the like having the surface thereof covered with colorants such as titanium oxide, iron oxide, silicon oxide, iron blue, chromium oxide, carmine, and organic pigments.

Various surface treatments such as a water-repellent treatment and a water-repellent/oil-repellent treatment may be given to those color materials by ordinary methods. The color material can be contained in an amount of 0.1 to 20% by weight in the oil-based cosmetic preparation.

Further, in addition to the above components, the oil-based cosmetic preparation of the present invention can contain components typically used for a cosmetic preparation, e.g., surfactants, alcohols, polyols, polymer compounds, ultraviolet light absorbers, antioxidants, dyes, perfumes, dyestuffs, stain-proofing agents, moisture-proof agents, and water.

The oil-based cosmetic preparation of the present invention can be produced by an ordinary method, and its dosage form may be any of a solid, a semisolid, a gel, or a liquid.

The oil-based cosmetic preparation of the present invention exhibits a normal stress in the measurement of viscoelasticity. The normal stress is a stress which occurs in a direction perpendicular to a shear face and acts to press and extend the face when a shear is given to a material. Specifically, the cosmetic preparation is mashed in a glass petri dish using a spatula and kneaded until lumps disappear. Subsequently, using a rotary mode viscoelasticity measurement apparatus (e.g., MCR-301 manufactured by Anton Paar GmbH), the viscoelasticity of the cosmetic preparation is measured in a cone plate (CP25-2) having a diameter of 25 mm at 30° C. at shear rates between $0.001\ s^{-1}$ and $1,000\ s^{-1}$. When the shear rates between $0.001\ s^{-1}$ and $1,000\ s^{-1}$ are divided equally into 19 points on a logarithmic axis and the viscoelasticity is measured from a low shear rate side, a first normal stress difference Ni of 10 Pa or more is observed until the shear rate is $1,000\ s^{-1}$. A range of the normal stress is preferably 50 to 10,000 Pa, more preferably 100 to 5,000 Pa, and even more preferably 300 to 3,000 Pa at a shear rate of $1,000\ s^{-1}$. When the normal stress is less than 50 Pa, the moist feeling is reduced and roughness tends to be felt. Meanwhile, when the normal stress exceeds 10,000 Pa, the feel becomes heavy and a stringy property occurs in some cases.

The oily cosmetics of the present invention include cosmetics for use on skin, lips, eyelashes, nails, and hair, and cosmetics that contain an oil agent as a continuous phase. The oily cosmetics may be used for lip cosmetics such as lip stick, lip gloss, and lip liner, mascara, eye liner, eye shadow, rouge, foundation, concealer, cream, milky lotion, beauty lotion, massage agent, deodorant, sunscreen, hair grower, hair colorant, hair wax, and hair foam, for example. In particular, the oily cosmetics are suitable for lip cosmetics.

The following examples further describe and demonstrate embodiments of the present invention. The examples are given solely for the purpose of illustration and are not to be construed as limitations of the present invention.

EXAMPLES

Production Example 1

Production of Cellulose Derivative 1

In chloroform under nitrogen at room temperature, to 5 g ($8.3\times10^{-6}$ mol) of hydroxypropyl cellulose (Celny M; manufactured by Nippon Soda Co., Ltd.), added were 50 mL of pyridine and 0.17 g (0.001 mol) of DMAP (dimethylaminopyridine), which were then dissolved. Subsequently, 27.9 g (0.101 mol) of palmitoyl chloride were added drop-wise over 0.5 hour. The mixture was then allowed to react at 50° C. for 15 hours, purified by precipitating in methanol, and dried to yield hydroxypropyl cellulose palmitate (weight average molecular weight: 870,000, average acyl substitution degree: 85 mol % in total hydroxyl groups).

(Measurement of Weight Average Molecular Weight)

The average molecular weight (Mw) of the polymer was measured by gel permeation chromatography (GPC) using Hitachi L-6000 model high performance liquid chromatography equipped with a Shodex RI SE-61 differential reflective index detector and two GPC columns GMHHR-H connected in series. A sample was adjusted to a concentration of 0.5 g/100 mL with an eluant, and 20 μL thereof were used. A solution of 1 mmol/L of dimethyl dodecylamine in chloroform was used as an eluant. The column temperature was 40° C. and the flow rate was 1.0 mL/min.

(Measurement of Average Acyl [Ester] Substitution Degree)

About 0.5 g of a cellulose derivative was precisely weighed, 4 mL of 5N sodium hydroxide and 25 mL of ethanol were added, and the mixture was refluxed at about 90° C. for 5 hours to completely hydrolyze the ester. After adding 30 g of water and refluxing at about 90° C. for 5 hours, the reaction mixture was neutralized with phosphoric acid, and it was confirmed using a pH test paper that the mixture was completely neutralized. Subsequently, 70 g of tetrahydrofuran were added to the reaction mixture, which was then stirred for 30 minutes and then left to stand at room temperature for 3 hours. The amount of fatty acid in the resulting supernatant was measured using Hitachi L-7000 model high performance liquid chromatography. Hitachi L-7400 (UV measurement) was used as the detector, and the measurement was performed at a wavelength of 210 nm. A solution of THF:water:phosphoric acid at 60:39:1 was used as the eluant.

Production Example 2

Production of Cellulose Derivative 2

In chloroform under nitrogen at room temperature, to 5 g ($8.3\times10^{-6}$ mol) of hydroxypropyl cellulose (Celny M; manufactured by Nippon Soda Co., Ltd.), added were 50 mL of pyridine and 0.17 g (0.001 mol) of DMAP (dimethylaminopyridine), which were then dissolved. Subsequently, 20.8 g (0.101 mol) of caproyl chloride were added drop-wise over 0.5 hour. The mixture was then allowed to react at 50° C. for 15 hours, purified by precipitating in methanol, and dried to yield hydroxypropyl cellulose caprate (weight average molecular weight: 700,000, average acyl substitution degree: 85 mol % in total hydroxyl groups).

Production Example 3

Production of Cellulose Derivative 3

In chloroform under nitrogen at room temperature, to 5 g ($8.3\times10^{-6}$ mol) of hydroxypropyl cellulose (Celny M; manufactured by Nippon Soda Co., Ltd.), added were 50 mL of pyridine and 0.17 g (0.001 mol) of DMAP (dimethylaminopyridine), which were then dissolved. Subsequently, 37.8 g (0.101 mol) of behenoyl chloride were added drop-wise over 0.5 hour. The mixture was then allowed to react at 50° C. for 15 hours, purified by precipitating in methanol, and dried to yield hydroxypropyl cellulose behenate (weight average molecular weight: 1,000,000, average acyl substitution degree: 80 mol % in total hydroxyl groups).

Production Example 4

Production of Cellulose Derivative 4

In chloroform under nitrogen at room temperature, to 5 g ($5 \times 10^{-6}$ mol) of hydroxypropyl cellulose (Celny SL; manufactured by Nippon Soda Co., Ltd.), added were 50 mL of pyridine and 0.17 g (0.001 mol) of DMAP (dimethylaminopyridine), which were then dissolved. Subsequently, 27.9 g (0.101 mol) of palmitoyl chloride were added drop-wise over 0.5 hour. The mixture was then allowed to react at 50° C. for 15 hours, purified by precipitating in methanol, and dried to yield hydroxypropyl cellulose palmitate (weight average molecular weight: 150,000, average acyl substitution degree: 80 mol in total hydroxyl groups).

Production Example 5

Production of Cellulose Derivative 5

In chloroform under nitrogen at room temperature, to 8.3 g (0.013 mol) of hydroxypropyl cellulose (Celny H; manufactured by Nippon Soda Co., Ltd.), added were 50 mL of pyridine and 0.17 g (0.001 mol) of DMAP (dimethylaminopyridine), which were then dissolved. Subsequently, 30.5 g (0.101 mol) of palmitoyl chloride were added drop-wise over 0.5 hour. The mixture was then allowed to react at 50° C. for 15 hours, purified by precipitating in methanol (or ethanol), and dried to yield hydroxypropyl cellulose palmitate (weight average molecular weight: 1,500,000, average acyl substitution degree: 70 mol % in total hydroxyl groups).

Production Example 6

Production of Cellulose Derivative 6

In chloroform under nitrogen at room temperature, to 5 g ($8.3 \times 10^{-6}$ mol) of hydroxypropyl cellulose (Celny M; manufactured by Nippon Soda Co., Ltd.), added were 50 mL of pyridine and 0.17 g (0.001 mol) of DMAP (dimethylaminopyridine), which were then dissolved. Subsequently, 9.0 g (0.101 mol) of acetyl chloride were added drop-wise over 0.5 hour. The mixture was then allowed to react at 50° C. for 15 hours, purified by precipitating in methanol, and dried to yield hydroxypropyl cellulose acetate (weight average molecular weight: 700,000, average acyl substitution degree: 85 mol % in total hydroxyl groups).

Production Example 7

Production of Cellulose Derivative 7

In chloroform under nitrogen at room temperature, to 5 g ($8.3 \times 10^{-6}$ mol) of hydroxypropyl cellulose (Celny M; manufactured by Nippon Soda Co., Ltd.), added were 50 mL of pyridine and 0.17 g (0.001 mol) of DMAP (dimethylaminopyridine), which were then dissolved. Subsequently, 9.0 g (0.031 mol) of palmitoyl chloride were added drop-wise over 0.5 hour. The mixture was then allowed to react at 50° C. for 15 hours, purified by precipitating in methanol, and dried to yield hydroxypropyl cellulose palmitate (weight average molecular weight: 750,000, average acyl substitution degree: 30 mol % in total hydroxyl groups).

Production Example 8

Production of Cellulose Derivative 8

In chloroform under nitrogen at room temperature, to 10 g ($16.6 \times 10^{-6}$ mol) of hydroxypropyl cellulose (Celny M; manufactured by Nippon Soda Co., Ltd.), added were 100 g of pyridine (1.26 mol), which were then dissolved. Subsequently, 40 g (0.138 mol) of palmitoyl chloride were added drop-wise over 0.5 hour. The mixture was then allowed to react at 50° C. for 15 hours, purified by precipitating in methanol, and dried to yield hydroxypropyl cellulose palmitate (weight average molecular weight: 800,000, average acyl substitution degree: 70 mol % in total hydroxyl groups).

Production Example 9

Production of Cellulose Derivative 9

In chloroform under nitrogen at room temperature, to 10 g ($16.6 \times 10^{-6}$ mol) of hydroxypropyl cellulose (Celny M; manufactured by Nippon Soda Co., Ltd.), added were 100 g of pyridine (1.26 mol), which were then dissolved. Subsequently, 55 g (0.189 mol) of palmitoyl chloride were added drop-wise over 0.5 hour. The mixture was then allowed to react at 50° C. for 15 hours, purified by precipitating in methanol, and dried to yield hydroxypropyl cellulose palmitate (weight average molecular weight: 900,000, average acyl substitution degree: 95 mol % in total hydroxyl groups).

Examples 1 to 12 and Comparative Examples 1 to 4

Oil-based cosmetic preparations having a composition shown in Table 1 were produced. The normal stress was measured, and the spreadability and compatibility upon application and the smoothness, non-sticky feeling, and application feeling immediately after application and after time were evaluated. Results are also shown in Table 1.

(Production Method)

The cellulose derivative, isotridecyl isononanoate, and hydrogenated polydecene were dissolved with heating at 80° C. and mixed uniformly to obtain an oil-based cosmetic preparation.

(Evaluation Method)

(1) Normal Stress

Preparation of Sample: the Oil-Based Cosmetic Preparation was mashed in a glass petri dish using a spatula and kneaded until lumps disappeared.

Measurement instrument: Rotary mode viscoelasticity measurement apparatus (MCR-301 manufactured by Anton Paar GmbH)

Jig: Cone plate having a diameter of 25 mm (CP25-2)

Measurement temperature: 30° C.

The sample was sandwiched with the plates, and the stress was measured on 19 points obtained by equally dividing the range of shear rates between 0.001 $s^{-1}$ and 1,000 $s^{-1}$ on a logarithmic scale into 19 points. A first normal stress difference Ni when the shear rate was 1,000 $s^{-1}$ was obtained.

(2) Spreadability Upon Application (Sensory Evaluation)

Ten special panelists sensorially evaluated the spreadability of each oil-based cosmetic preparation upon application onto the skin. The evaluation was shown by the number of the panelists who had evaluated that the oil-based cosmetic composition was good.

(3) Compatibility Upon Application (Sensory Evaluation)

Ten special panelists sensorially evaluated the compatibility of each oil-based cosmetic preparation upon application onto the skin. The evaluation was shown by the number of the panelists who had evaluated that the oil-based cosmetic composition was good.

(4) Smoothness (Sensory Evaluation)

Ten special panelists sensorially evaluated the smoothness of the applied area immediately and 3 hours after applying each oil-based cosmetic preparation. The evaluation was shown by the number of the panelists who had evaluated that the oil-based cosmetic preparation was good.

(5) Non-Sticky Feeling (Sensory Evaluation)

Ten special panelists sensorially evaluated the non-sticky feeling immediately and 3 hours after applying each oil-based cosmetic preparation. The evaluation was shown by the number of the panelists who had evaluated that the oil-based cosmetic preparation was good (had a non-sticky feeling).

(6) Application Feeling (Sensory Evaluation)

Ten special panelists sensorially evaluated application feeling immediately and 3 hours after applying each oil-based cosmetic preparation. The evaluation was shown by the number of the panelists who had evaluated that the oil-based cosmetic preparation was good (had application feeling).

TABLE 1

| Component (% by weight) | Example 1 | 2 | 3 | 4 | 5 | 6 | 7 | 8 |
|---|---|---|---|---|---|---|---|---|
| Cellulose derivative 1 | 10 | 10 | 10 | 10 | 10 | 10 | 10 | 10 |
| Cellulose derivative 2 | | | | | | | | |
| Cellulose derivative 3 | | | | | | | | |
| Cellulose derivative 4 | | | | | | | | |
| Cellulose derivative 5 | | | | | | | | |
| Cellulose derivative 6 | | | | | | | | |
| Cellulose derivative 7 | | | | | | | | |
| Isotridecyl isononanoate | 80 | 75 | 70 | 60 | 45 | 30 | 22.5 | 18 |
| Hydrogenated polydecene (number average molecular weight: 443) | 10 | 15 | 20 | 30 | 45 | 60 | 67.5 | 72 |
| Total | 100 | 100 | 100 | 100 | 100 | 100 | 100 | 100 |
| (B)/(C) | 8/1 | 5/1 | 3.5/1 | 2/1 | 1/1 | 1/2 | 1/3 | 1/4 |
| Normal stress (Pa) | 3,000 | 3,050 | 3,200 | 3,500 | 3,800 | 4,000 | 5,000 | 5,500 |
| Spreadability upon application | 8 | 8 | 9 | 9 | 8 | 7 | 7 | 5 |
| Compatibility upon application | 5 | 6 | 7 | 9 | 7 | 6 | 7 | 5 |
| Smoothness (immediately after application) | 6 | 6 | 7 | 10 | 10 | 9 | 6 | 5 |
| (after 3 hours) | 4 | 6 | 7 | 7 | 7 | 6 | 6 | 5 |
| Non-sticky feeling (immediately after application) | 9 | 9 | 8 | 8 | 7 | 6 | 5 | 4 |
| (after 3 hours) | 7 | 7 | 7 | 6 | 6 | 5 | 5 | 5 |
| Application feeling (immediately after application) | 5 | 6 | 6 | 7 | 7 | 8 | 7 | 6 |
| (after 3 hours) | 3 | 5 | 5 | 6 | 5 | 5 | 4 | 3 |

| Component (% by weight) | Example 9 | 10 | 11 | 12 | Comparative Example 1 | 2 | 3 | 4 |
|---|---|---|---|---|---|---|---|---|
| Cellulose derivative 1 | | | | | 10 | 10 | | |
| Cellulose derivative 2 | 10 | | | | | | | |
| Cellulose derivative 3 | | 10 | | | | | | |
| Cellulose derivative 4 | | | 10 | | | | | |
| Cellulose derivative 5 | | | | 10 | | | | |
| Cellulose derivative 6 | | | | | | | 10 | |
| Cellulose derivative 7 | | | | | | | | 10 |
| Isotridecyl isononanoate | 60 | 60 | 60 | 60 | 90 | — | 60 | 60 |
| Hydrogenated polydecene (number average molecular weight: 443) | 30 | 30 | 30 | 30 | — | 90 | 30 | 30 |
| Total | 100 | 100 | 100 | 100 | 100 | 100 | 100 | 100 |
| (B)/(C) | 2/1 | 2/1 | 2/1 | 2/1 | — | — | 2/1 | 2/1 |
| Normal stress (Pa) | 1,500 | 800 | 700 | 6,000 | 2,500 | 7,500 | 0 | 0 |
| Spreadability upon application | 9 | 7 | 9 | 6 | 6 | 3 | 0 | 0 |
| Compatibility upon application | 8 | 8 | 9 | 5 | 4 | 3 | 0 | 0 |
| Smoothness (immediately after application) | 8 | 7 | 6 | 6 | 5 | 5 | 0 | 0 |
| (after 3 hours) | 6 | 6 | 5 | 6 | 3 | 4 | 0 | 0 |
| Non-sticky feeling (immediately after application) | 8 | 6 | 9 | 5 | 9 | 4 | 0 | 0 |
| (after 3 hours) | 8 | 6 | 6 | 5 | 7 | 5 | 0 | 0 |
| Application feeling (immediately after application) | 4 | 6 | 4 | 6 | 4 | 6 | 0 | 0 |
| (after 3 hours) | 5 | 6 | 4 | 7 | 3 | 3 | 0 | 0 |

Examples 13 to 19

Oil-based cosmetic preparations having a composition shown in Table 2 were produced. In the same ways as those in Examples 1 to 12, the normal stress was measured, and the spreadability and compatibility upon application and the smoothness, non-sticky feeling, and application feeling immediately after application and over time were evaluated. Results are also shown in Table 2.

(Production Method)

The cellulose derivative 1, isotridecyl isononanoate, hydrogenated polydecene, and hydrogenated polyisobutene were dissolved by heating at 80° C. and mixed uniformly to obtain an oil-based cosmetic preparation.

TABLE 2

| Component (% by weight) | Example 13 | 14 | 15 | 16 | 17 | 18 | 19 |
|---|---|---|---|---|---|---|---|
| Cellulose derivative 1 | 10 | 10 | 10 | 10 | 10 | 10 | 10 |
| Isotridecyl isononanoate | 60 | 60 | 80 | 70 | 60 | 80 | 60 |
| Hydrogenated polydecene (number average molecular weight: 443) | 20 | 10 | | | 10 | | 20 |
| Hydrogenated polyisobutene (number average molecular weight: 1,000) | | | | 20 | 20 | | |
| Hydrogenated polyisobutene (number average molecular weight: 1,350) | 10 | 20 | 10 | | | | |
| Hydrogenated polyisobutene (number average molecular weight: 2,650) | | | | | | 10 | 10 |
| Total | 100 | 100 | 100 | 100 | 100 | 100 | 100 |
| (B)/(C) | 2/1 | 2/1 | 8/1 | 7/2 | 2/1 | 8/1 | 2/1 |
| Normal stress (Pa) | 4,000 | 5,500 | 4,500 | 4,000 | 5,500 | 5,000 | 5,500 |
| Spreadability upon application | 9 | 9 | 7 | 8 | 9 | 8 | 9 |
| Compatibility upon application | 8 | 8 | 6 | 7 | 8 | 7 | 8 |
| Smoothness | | | | | | | |
| (immediately after application) | 9 | 9 | 9 | 9 | 10 | 7 | 9 |
| (after 3 hours) | 10 | 10 | 10 | 10 | 10 | 8 | 8 |
| Non-sticky feeling | | | | | | | |
| (immediately after application) | 8 | 6 | 8 | 8 | 9 | 7 | 8 |
| (after 3 hours) | 9 | 8 | 9 | 9 | 10 | 8 | 9 |
| Application feeling | | | | | | | |
| (immediately after application) | 8 | 9 | 9 | 9 | 10 | 10 | 10 |
| (after 3 hours) | 9 | 10 | 8 | 8 | 10 | 9 | 10 |

Examples 20 and 21

Lip Stick

Lip sticks each having the composition shown in Table 3 were produced. The normal stress was measured, and the spreadability and compatibility upon application and the smoothness, non-sticky feeling, and application feeling immediately after application and over time were evaluated in the same manner as in Examples 1 to 12. Note that, each evaluation was performed on lips. The smoothness and non-sticky feeling were evaluated when the lip stick was applied on the lips and the lips were rubbed together. The results are also shown in Table 3.

(Production Method)

Base materials other than a color material were dissolved by heating and mixed uniformly. A raw material for the color material was added to the mixture. The resultant was dispersed uniformly using a disperser in a heated state, defoamed, and then run into a mold where molding was performed to obtain a lipstick.

TABLE 3

| Component (% by weight) | Example 20 | 21 |
|---|---|---|
| Cellulose derivative 1 | 4 | 4 |
| Microcrystalline wax | 5 | 5 |
| Paraffin | 2 | 2 |
| Ceresin | 3 | 3 |
| Petrolatum | 3 | 3 |
| Phytosteryl oleate | 3 | 3 |
| Isotridecyl isononanoate | 10 | 10 |
| Glyceryl tri(caprylate/caprate) | 8 | 6 |
| Diisostearyl malate | 10 | 10 |
| Jojoba oil | 10 | 10 |
| Squalane (molecular weight: 212) | 8 | 2 |
| Hydrogenated polydecene (number average molecular weight: 443) | 5 | 3 |
| Hydrogenated polyisobutene (number average molecular weight: 1350) | 15 | 25 |
| Octyldodecanol | 5 | 5 |
| Titanium oxide | 3 | 3 |
| Iron oxide | 1 | 1 |
| Red No. 201 | 0.2 | 0.2 |
| Red No. 202 | 0.3 | 0.3 |
| Yellow No. 4 Al | 0.5 | 0.5 |
| Mica titanium | 4 | 4 |
| Total | 100 | 100 |
| (B)/(C) | 38/28 | 36/30 |
| Normal stress (Pa) | 2,000 | 3,000 |
| Spreadability upon application | 9 | 9 |
| Compatibility upon application | 9 | 9 |
| Smoothness | | |
| (immediately after application) | 10 | 10 |
| (after 3 hours) | 8 | 10 |
| Non-sticky feeling | | |
| (immediately after application) | 8 | 7 |
| (after 3 hours) | 8 | 7 |
| Application feeling | | |
| (immediately after application) | 9 | 10 |
| (after 3 hours) | 7 | 9 |

Example 22

Lip Stick

A lip stick having the composition shown below was produced.

Note that, a crystallization temperature of a paste oil solution used in the following example was measured by the following method.

(Measurement of Crystallization Temperature of Paste Oil Solution)

A sample (36 mg) was taken, placed in an aluminum cell for DSC (AL70-CAPSULE; Epolead Service Inc.), and closed with a lid. A thermal capacity analysis of the sample was performed on DSC EXSTAR6100 (Seiko Instruments Inc.) using as a reference α-alumina in the same amount. First, the temperature was raised up to 120° C. at a speed of 10° C./min., kept at 120° C. for 10 minutes, and then cooled at a speed of 5° C./min. The onset temperature of exothermic peak during cooling was designated as the crystallization temperature.

(Component)

| | |
|---|---|
| (1) Cellulosederivative1 (ProductionExample1) | 3.0 (weight %) |
| (2) Microcrystalline wax (Multiwax W-445, manufactured by SONNEBORN INC.) | 3.0 |
| (3) Paraffin (HNP-9, manufactured by NIPPON SEIRO CO., LTD.) | 5.0 |
| (4) Ceresin (Ceresin #810, (manufactured by NIKKO RICA CORPORATION) | 4.0 |
| (5) Isotridecyl isononanoate | 10.0 |
| (6) Neopentylglycol dicaprate | 20.0 |
| (7) Diisostearyl malate | 10.0 |
| (8) Jojoba oil | 10.0 |
| (9) Squalane | 6.0 |
| (10) Hydrogenated polydecene (SILKFLO 364NF, (manufactured by LIPO CHEMICALS INC.) | 6.0 |
| (11) Hydrogenated polyisobutene (number average molecular weight; 1,350) (PARLEAM 24, manufactured by NOF Corp.) | 5.0 |
| (12) Octyldodecanol | 5.0 |
| (13) Titanium oxide | 1.0 |
| (14) Iron oxide | 0.3 |
| (15) Red No. 201 | 0.2 |
| (16) Red No. 202 | 0.4 |
| (17) Blue No. 1 Al | 0.1 |
| (18) Yellow No. 4 Al | 1.0 |
| (19) Dimer dilinoleic acid dimer dilinoleyl bis(behenyl/isostearyl/phytosteryl) (Plandool-G, manufactured by NIPPON FINE CHEMICAL CO., LTD., crystallization temperature: 28.6° C.) | 10.0 |

(Production Method)

Base materials (other than a color material) were melted with heating at 90° C. and mixed uniformly. Subsequently, a raw material for the color material was added to the mixture. The resultant was dispersed uniformly using a disperser in a heated state, defoamed, and then run into a mold to obtain a lip stick.

The obtained lip stick was excellent in easiness to spread upon application, luster immediately after application and after time, and a non-sticky feeling immediately after application and after time.

Example 23

A lipstick is obtained in the same manner as in Example 22, except that the component (19) was replaced with phytosteryl oleate (Salacos PO(T), manufactured by THE NISSHIN OIL-LIO GROUP., LTD., crystallization temperature: 26.4° C.).

The obtained lip stick is excellent in easiness to spread upon application, luster immediately after application and after time, and non-sticky feeling immediately after application and after time.

Example 24

A lip stick is obtained in the same manner as in Example 22, except that the component (19) was replaced with cholesteryl isostearate (EXCEPARL IS-CE, manufactured by Kao Corporation, crystallization temperature: 31.0° C.).

The obtained lip stick is excellent in easiness to spread upon application, luster immediately after application and after time, and non-sticky feeling immediately after application and after time.

Example 25

A lip stick is obtained in the same manner as in Example 22, except that the component (19) was replaced with macadamia nuts oil polyglyceryl-6 esters behenate (S-FACE VL-211, manufactured by SAKAMOTO YAKUHIN KOGYO CO., LTD., crystallization temperature: 41.7° C.)

The obtained lip stick is excellent in easiness to spread upon application, luster immediately after application and after time, and non-sticky feeling immediately after application and after time.

Example 26

A lipstick is obtained in the same manner as in Example 22, except that the component (19) was replaced with dipentaerythrityl hexahydroxystearate (COSMOL 168M, manufactured by THE NISSHIN OILLIO GROUP, LTD., crystallization temperature: 24.3° C.).

The obtained lip stick is excellent in easiness to spread upon application, luster immediately after application and after time, and non-sticky feeling immediately after application and after time.

Examples 27 to 41, Comparative Examples 5 to 6

Lip sticks each having the composition shown in Tables 4 to 6 were produced. The normal stress was measured, and the easiness to spread, amount of glittering, smoothness, and non-roughness when each lip stick was applied on the lips were evaluated. The results are also shown in Tables 4 to 5.

(Production Method)

Base materials (other than a color material) were melted with heating at 80° C. and mixed uniformly. Subsequently, a raw material for the color material was added to the mixture. The resultant was dispersed uniformly using a disperser in a heated state, defoamed, and then run into a mold to obtain a lip stick.

(Evaluation Method)

(1) Normal Stress

Preparation of Sample: the Lip Stick was Mashed in a Glass petri dish using a spatula and kneaded until lumps disappeared.

Measurement instrument: Rotary mode viscoelasticity measurement apparatus (MCR-301 manufactured by Anton Paar GmbH)

Jig: Cone plate having a diameter of 25 mm (CP25-2)

Measurement temperature: 30° C.

The sample was sandwiched with the plates, and the stress was measured on 19 points obtained by equally dividing the range of shear rates between 0.001 $s^{-1}$ and 1,000 $s^{-1}$ on a logarithmic scale. A first normal stress difference Ni when the shear rate was 1,000 $s^{-1}$ was obtained.

(2) Easiness to Spread (Sensory Evaluation)

Ten special panelists sensorially evaluated the easiness to spread of each lip stick applied onto the lips. The evaluation was shown by the number of the panelists who had evaluated that the lip stick was good (easy to spread).

(3) Amount of Glittering (Sensory Evaluation)

Ten special panelists sensorially evaluated the amount of glittering immediately and 3 hours after applying each lip stick. The evaluation was shown by the number of the panelists who had evaluated that the lip stick was good (had a high glittering property).

(4) Non-Roughness (Sensory Evaluation)

Ten special panelists sensorially evaluated the non-roughness immediately and 3 hours after applying each lip stick. The evaluation was shown by the number of the panelists who had evaluated that the lip stick was good (had no roughness).

(5) Smoothness (Sensory Evaluation)

Ten special panelists sensorially evaluated the smoothness immediately and 3 hours after applying each lip stick. The evaluation was shown by the number of the panelists who had evaluated that the lip stick was good (had smoothness).

TABLE 4

| Component (% by weight) | Example | | | | | | | | | |
|---|---|---|---|---|---|---|---|---|---|---|
| | 27 | 28 | 29 | 30 | 31 | 32 | 33 | 34 | 35 | 36 |
| Cellulose derivative 1 (Production Example 1) | 1 | 1.5 | | | | | | | 0.1 | 10 |
| Cellulose derivative 2 (Production Example 2) | | | 2 | | | | | | | |
| Cellulose derivative 3 (Production Example 3) | | | | 2 | | | | | | |
| Cellulose derivative 4 (Production Example 4) | | | | | 5 | | | | | |
| Cellulose derivative 5 (Production Example 5) | | | | | | 1 | | | | |
| Cellulose derivative 8 (Production Example 8) | | | | | | | 1 | | | |
| Cellulose derivative 9 (Production Example 9) | | | | | | | | 1 | | |
| Microcrystalline wax *1 | 5 | 5 | 5 | 5 | 5 | 5 | 5 | 5 | 5 | 5 |
| Paraffin *2 | 3 | 3 | 3 | 3 | 3 | 3 | 3 | 3 | 3 | 3 |
| Ceresin *3 | 3 | 3 | 3 | 3 | 3 | 3 | 3 | 3 | 3 | 3 |
| Petrolatum | 2 | 2 | 2 | 2 | 2 | 2 | 2 | 2 | 2 | 2 |
| Phytosteryl oleate *4 | 2 | 2 | 2 | 2 | 2 | 2 | 2 | 2 | 2 | 2 |
| Isotridecyl isononanoate | 10 | 10 | 10 | 10 | 10 | 10 | 10 | 10 | 10 | 10 |
| Neopentyl glycol dicaprate | 15 | 14.5 | 14 | 14 | 11 | 15 | 15 | 15 | 15.9 | 6 |
| Diisostearyl malate | 10 | 10 | 10 | 10 | 10 | 10 | 10 | 10 | 10 | 10 |
| Jojoba oil *5 | 10 | 10 | 10 | 10 | 10 | 10 | 10 | 10 | 10 | 10 |
| Squalane | 5 | 5 | 5 | 5 | 5 | 5 | 5 | 5 | 5 | 5 |
| Hydrogenated polydecene *6 (number average molecular weight: 443) | 5 | 5 | 5 | 5 | 5 | 5 | 5 | 5 | 5 | 5 |
| Hydrogenated polyisobutene *7 (number average molecular weight: 1350) | 20 | 20 | 20 | 20 | 20 | 20 | 20 | 20 | 20 | 20 |
| Octyldodecanol | 3 | 3 | 3 | 3 | 3 | 3 | 3 | 3 | 3 | 3 |
| Titanium oxide | 1 | 1 | 1 | 1 | 1 | 1 | 1 | 1 | 1 | 1 |
| Iron oxide | 0.3 | 0.3 | 0.3 | 0.3 | 0.3 | 0.3 | 0.3 | 0.3 | 0.3 | 0.3 |
| Red No. 201 | 0.2 | 0.2 | 0.2 | 0.2 | 0.2 | 0.2 | 0.2 | 0.2 | 0.2 | 0.2 |
| Red No. 202 | 0.4 | 0.4 | 0.4 | 0.4 | 0.4 | 0.4 | 0.4 | 0.4 | 0.4 | 0.4 |
| Blue No. 1 Al | 0.1 | 0.1 | 0.1 | 0.1 | 0.1 | 0.1 | 0.1 | 0.1 | 0.1 | 0.1 |
| Yellow No. 4 Al | 1 | 1 | 1 | 1 | 1 | 1 | 1 | 1 | 1 | 1 |
| Titanium oxide/silicic anhydride-coated glass powder (average thickness; 1 μm, average particle diameter; 120 μm) *8 | 3 | | 3 | 3 | 3 | 3 | 3 | 3 | 3 | 3 |
| PET/polyethylene isoterephthalate-laminated film powder (average thickness; 19 μm, average particle diameter; 200 μm) *9 | | 3 | | | | | | | | |
| Titanium oxide/silicic anhydride-coated glass powder (average thickness; 1 μm, average particle diameter; 40 μm) *10 | | | | | | | | | | |
| Mica titanium (average particle diameter; 5 to 25 μm) *11 | | | | | | | | | | |
| Total | 100 | 100 | 100 | 100 | 100 | 100 | 100 | 100 | 100 | 100 |
| (B)/(C) | 1.5/1 | 1.5/1 | 1.5/1 | 1.5/1 | 1.4/1 | 1.5/1 | 1.5/1 | 1.5/1 | 1.5/1 | 1.2/1 |
| Normal stress (Pa) | 1,200 | 1,300 | 600 | 500 | 300 | 1,500 | 1,400 | 1,100 | 400 | 1,400 |
| Easiness to spread | 10 | 10 | 8 | 8 | 9 | 8 | 9 | 10 | 9 | 5 |
| Amount of Glittering: immediately after application | 10 | 10 | 10 | 10 | 10 | 10 | 10 | 10 | 10 | 10 |
| after 3 hours | 10 | 10 | 8 | 7 | 8 | 10 | 10 | 10 | 7 | 10 |
| Non-roughness: immediately after application | 10 | 9 | 7 | 7 | 8 | 10 | 10 | 9 | 6 | 10 |
| after 3 hours | 10 | 10 | 8 | 8 | 8 | 10 | 10 | 9 | 7 | 10 |
| Smoothness: immediately after application | 10 | 10 | 8 | 8 | 7 | 9 | 10 | 9 | 9 | 10 |
| after 3 hours | 10 | 10 | 8 | 8 | 7 | 10 | 10 | 9 | 8 | 9 |

TABLE 5

| Component (% by weight) | Example 37 | Example 38 | Example 39 | Example 40 | Example 41 | Example 42 | Example 43 | Comparative Example 5 | Comparative Example 6 |
|---|---|---|---|---|---|---|---|---|---|
| Cellulose derivative 1 (Production Example 1) | 1 | 1 | 1 | 1 | 1 | 1 | 1 | | |
| Cellulose derivative 2 (Production Example 2) | | | | | | | | | |
| Cellulose derivative 3 (Production Example 3) | | | | | | | | | |
| Cellulose derivative 4 (Production Example 4) | | | | | | | | | |
| Cellulose derivative 5 (Production Example 5) | | | | | | | | | |
| Microcrystalline wax *1 | 5 | 5 | 5 | 5 | 5 | 5 | 5 | 5 | 5 |
| Paraffin *2 | 3 | 3 | 3 | 3 | 3 | 3 | 3 | 3 | 3 |
| Ceresin *3 | 3 | 3 | 3 | 3 | 3 | 3 | 3 | 3 | 3 |
| Petrolatum | 2 | 2 | 2 | 2 | 2 | 2 | 2 | 2 | 2 |
| Phytosteryl oleate *4 | 2 | 2 | 2 | 2 | 2 | 2 | 2 | 2 | 2 |
| Isotridecyl isononanoate | 5 | 10 | 10 | 10 | 10 | 10 | 10 | 10 | 10 |
| Neopentyl glycol dicaprate | 3 | 13 | 17.8 | 17.5 | 8 | 3 | 11 | 16 | 16 |
| Diisostearyl malate | 5 | 10 | 10 | 10 | 10 | 10 | 10 | 10 | 10 |
| Jojoba oil *5 | 5 | 10 | 10 | 10 | 10 | 10 | 10 | 10 | 10 |
| Squalane | 15 | 5 | 5 | 5 | 5 | 5 | 5 | 5 | 5 |
| Hydrogenated polydecene *6 (number average molecular weight: 443) | 10 | 5 | 5 | 5 | 5 | 5 | 5 | 5 | 5 |
| Hydrogenated polyisobutene *7 (number average molecular weight: 1,350) | 30 | 20 | 20 | 20 | 20 | 20 | 20 | 20 | 20 |
| Octyldodecanol | 5 | 3 | 3 | 3 | 3 | 3 | 5 | 3 | 3 |
| Titanium oxide | 1 | 1 | 1 | 1 | 1 | 1 | 1 | 1 | 1 |
| Iron oxide | 0.3 | 0.3 | 0.3 | 0.3 | 0.3 | 0.3 | 0.3 | 0.3 | 0.3 |
| Red No. 201 | 0.2 | 0.2 | 0.2 | 0.2 | 0.2 | 0.2 | 0.2 | 0.2 | 0.2 |
| Red No. 202 | 0.4 | 0.4 | 0.4 | 0.4 | 0.4 | 0.4 | 0.4 | 0.4 | 0.4 |
| Blue No. 1 Al | 0.1 | 0.1 | 0.1 | 0.1 | 0.1 | 0.1 | 0.1 | 0.1 | 0.1 |
| Yellow No. 4 Al | 1 | 1 | 1 | 1 | 1 | 1 | 1 | 1 | 1 |
| Titanium oxide/silicic anhydride-coated glass powder (average thickness; 1 μm, average particle diameter; 120 μm) *8 | 3 | | 0.2 | 0.5 | 10 | 15 | | 3 | |
| PET/polyethylene isoterephthalate-laminated film powder (average thickness; 19 μm, average particle diameter; 200 μm) *9 | | | | | | | | | 3 |
| Titanium oxide/silicic anhydride-coated glass powder (average thickness; 1 μm, average particle diameter; 40 μm) *10 | | 5 | | | | | | | |
| Mica titanium (average particle diameter; 5 to 25 μm) *11 | | | | | | | 5 | | |
| Total | 100 | 100 | 100 | 100 | 100 | 100 | 100 | 100 | 100 |
| (B)/(C) | 1/3.1 | 1.4/1 | 1.6/1 | 1.6/1 | 1.3/1 | 1.1/1 | 1.4/1 | 1.5/1 | 1.5/1 |
| Normal stress (Pa) | 1,100 | 1,200 | 1,200 | 1,200 | 1,300 | 1,400 | 1,200 | 0 | 0 |
| Easiness to spread | 3 | 10 | 10 | 10 | 8 | 7 | 10 | 4 | 3 |
| Amount of Glittering: immediately after application | 10 | 8 | 6 | 7 | 10 | 10 | 4 | 10 | 10 |
| after 3 hours | 6 | 7 | 5 | 6 | 10 | 10 | 3 | 6 | 7 |
| Non-roughness: immediately after application | 9 | 10 | 10 | 10 | 7 | 6 | 10 | 2 | 1 |
| after 3 hours | 9 | 10 | 10 | 10 | 8 | 7 | 10 | 3 | 2 |
| Smoothness: immediately after application | 9 | 10 | 10 | 10 | 7 | 7 | 10 | 5 | 4 |
| after 3 hours | 9 | 10 | 10 | 10 | 8 | 8 | 10 | 4 | 3 |

*1: Multiwax W-445 (manufactured by SONNEBORN, Inc.)
*2: HNP-9 (manufactured by Nippon Seiro Co., Ltd.)
*3: Ceresin #810 (manufactured by Nikko Rica Corporation)
*4: Salacos PO(T) (manufactured by THE NISSHIN OILLIO GROUP, LTD.)
*5: Purified jojoba oil (manufactured by Koei Kogyo Co., Ltd.)
*6: SILKFLO 364 NF (manufactured by LIPO CHEMICALS, Inc.)
*7: PARLEAM 24 (manufactured by NOF Corporation)
*8: Metashine MC1120RRS1 (manufactured by Nippon Sheet Glass Co., Ltd.)
*9: New Aurora Flake (19) Red (manufactured by KAKUHACHI Co., Ltd.)
*10: Metashine MC1040RRS1 (manufactured by Nippon Sheet Glass Co., Ltd.)
*11: PRESTIGE Silk Red (manufactured by ECKART)

The invention claimed is:

1. An oil-based cosmetic preparation comprising components (A), (B), and (C):
   (A) 0.8 to 15% by weight of a cellulose compound having a cellulose skeleton in a main chain, wherein 67 mol % to 100 mol % of the total hydroxyl groups are substituted with a group —O-M-R, wherein M represents $CH_2$ or a carbonyl group C=O, and R represents a straight alkyl group having 9 to 21 carbon atoms, wherein said cellulose compound having a cellulose skeleton in a main chain has the cellulose skeleton:

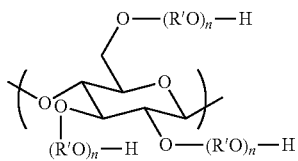

wherein R' is an ethylene group or a propylene group, n represents the average addition mole number of R'O per glucose unit and is from 1 to 4;
   (B) 10 to 80% by weight of an ester oil which is liquid at 25° C.; and
   (C) 5 to 60% by weight of a hydrocarbon oil which is liquid at 25° C., wherein a weight ratio (B)/(C) of the component (B) to the component (C) is 8/1 to 1/4.

2. The oil-based cosmetic preparation according to claim 1, wherein the component (C) comprises a liquid hydrocarbon oil having a number average molecular weight of 1,000 to 5,000.

3. The oil-based cosmetic preparation according to claim 1, wherein the component (C) comprises a liquid hydrocarbon oil having a number average molecular weight of 700 or less and a liquid hydrocarbon oil having a number average molecular weight of 1,000 or more.

4. The oil-based cosmetic preparation according to claim 1, wherein the component (B) comprises a branched, saturated fatty acid ester.

5. The oil-based cosmetic preparation according to claim 1, having a normal stress of 50 to 10,000 Pa at a shear rate of 1,000 $s^{-1}$.

6. The oil-based cosmetic preparation according to claim 1, further comprising at least one paste oil solution (D) selected from the group consisting of
   a dimer acid ester, a dimer diol compound, a cholesterol fatty acid ester, a phytosterol fatty acid ester, a polyglycerine fatty acid ester, and a pentaerythritol fatty acid ester.

7. The oil-based cosmetic preparation according to claim 6, wherein the component (D) has a crystallization temperature measured by DSC of 20 to 55° C.

8. The oil-based cosmetic preparation according to claim 1, further comprising a glittering powder (E) having an average particle diameter of 30 to 500 μm.

9. The oil-based cosmetic preparation according to claim 8, wherein the glittering powder is a plate substrate having an average particle diameter of 30 to 500 μm and is covered with one or more kinds of color materials selected from metals, metal oxide, and organic pigments.

10. The oil-based cosmetic preparation according to claim 8, wherein the component (E) is a laminated powder having an average particle diameter of 30 to 500 μm.

11. The oil-based cosmetic preparation according to claim 1, wherein in (A) 70 mol % to 95 mol % of the total hydroxyl groups of said cellulose compound are substituted with the group —O-M-R.

12. The oil-based cosmetic preparation according to claim 1, wherein in (A) 80 mol % to 95 mol % of the total hydroxyl groups of said cellulose compound are substituted with the group —O-M-R.

13. The oil-based cosmetic preparation according to claim 1, wherein in (A) 70 mol % to 90 mol % of the total hydroxyl groups of said cellulose compound are substituted with the group —O-M-R.

14. The oil-based cosmetic preparation according to claim 1, wherein in (A) 80 mol % to 90 mol % of the total hydroxyl groups of said cellulose compound are substituted with the group —O-M-R.

* * * * *